(12) United States Patent
Itoh

(10) Patent No.: US 9,776,811 B2
(45) Date of Patent: *Oct. 3, 2017

(54) CONVEYING DEVICE

(71) Applicant: AOI SEIKI CO., LTD., Kumamoto-shi, Kumamoto-ken (JP)

(72) Inventor: Teruaki Itoh, Kumamoto (JP)

(73) Assignee: AOI SEIKI CO., LTD., Kumamoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/083,514

(22) Filed: Mar. 29, 2016

(65) Prior Publication Data

US 2016/0289011 A1    Oct. 6, 2016

(30) Foreign Application Priority Data

Mar. 31, 2015 (JP) .................. 2015-072929

(51) Int. Cl.
  *B65G 54/02* (2006.01)
  *B65G 33/04* (2006.01)
  (Continued)

(52) U.S. Cl.
  CPC ........... *B65G 54/02* (2013.01); *B65G 35/066* (2013.01); *B65G 37/00* (2013.01); *B65G 54/025* (2013.01);
  (Continued)

(58) Field of Classification Search
  CPC ........ B65G 33/04; B65G 54/02; B65G 35/06; B65G 35/063; B65G 2201/02; G01N 35/04; G01N 2035/0477; G01N 2035/0487
  (Continued)

(56) References Cited

U.S. PATENT DOCUMENTS 3,622,128 A * 11/1971 Geiser ..................... B01F 13/08
                                              366/144
5,377,816 A *  1/1995 Deligi ............... H01L 21/67709
                                              198/619
(Continued)

FOREIGN PATENT DOCUMENTS

CN    1513739    7/2004
CN    2905177    5/2007
(Continued)

OTHER PUBLICATIONS

Taiwanese Office Action issued in App. No. 105109514 dated Nov. 24, 2016 (w/ translation).
(Continued)

*Primary Examiner* — Mark A Deuble
(74) *Attorney, Agent, or Firm* — Nixon & Vanderhye P.C.

(57) ABSTRACT

A conveying device includes a carrier which includes a holder side member; a conveying passage which guides conveyance of the carrier; a spirally-shaped spiral member which is arranged below the carrier and extends along the conveying passage, the spiral member causing between the spiral member and the holder side member a first force which acts in a direction away from the holder side member or a second force which acts to draw in the holder side member; a partition wall portion which is provided between the carrier and the spiral member and partitions the carrier and the spiral member; and a rotary unit which rotates the spiral member axis-wise thereof.

1 Claim, 3 Drawing Sheets

(51) Int. Cl.
  *B65G 35/06* (2006.01)
  *B65G 37/00* (2006.01)
  *G01N 35/04* (2006.01)

(52) U.S. Cl.
  CPC ..... *G01N 35/04* (2013.01); *B65G 2201/0261* (2013.01); *G01N 2035/0406* (2013.01); *G01N 2035/0475* (2013.01); *G01N 2035/0477* (2013.01); *G01N 2035/0484* (2013.01); *G01N 2035/0487* (2013.01)

(58) Field of Classification Search
  USPC .......................................................... 198/619
  See application file for complete search history.

(56) References Cited

U.S. PATENT DOCUMENTS

| | | | |
|---|---|---|---|
| 5,881,649 A * | 3/1999 | Hasegawa | H01L 21/67709 104/166 |
| 5,906,262 A | 5/1999 | Miki | |
| 5,913,401 A * | 6/1999 | Tamura | H02K 49/102 198/619 |
| 6,251,232 B1 | 6/2001 | Aruga et al. | |
| 6,471,469 B2 | 10/2002 | Toffan et al. | |
| 6,561,343 B2 | 5/2003 | Miyauchi et al. | |
| 7,207,241 B2 * | 4/2007 | Itoh | B67B 7/00 53/381.4 |
| 7,264,111 B2 | 9/2007 | Veiner | |
| 8,261,905 B2 | 9/2012 | Kholodenko et al. | |
| 9,027,739 B2 | 5/2015 | Hosek | |
| 2002/0060134 A1 * | 5/2002 | Miyauchi | H01L 21/67709 198/619 |
| 2005/0271555 A1 * | 12/2005 | Itoh | B01L 9/06 422/400 |
| 2006/0278497 A1 * | 12/2006 | White | C23C 14/56 198/339.1 |
| 2009/0260457 A1 | 10/2009 | Itoh | |
| 2010/0226828 A1 | 9/2010 | Itoh | |
| 2013/0233673 A1 | 9/2013 | Itoh | |
| 2015/0226760 A1 * | 8/2015 | Itoh | B65G 33/04 198/657 |

FOREIGN PATENT DOCUMENTS

| | | |
|---|---|---|
| CN | 103303639 | 9/2013 |
| EP | 2 642 300 | 9/2013 |
| JP | 4-365666 A | 12/1992 |
| JP | 4522463 | 6/2010 |
| JP | 4522463 | 8/2010 |
| KR | 10-2013-0103408 | 9/2013 |
| TW | M444363 | 1/2013 |

OTHER PUBLICATIONS

Extended European Search Report issued in App. No. 16162361.6 dated Aug. 4, 2016.
Canadian Office Action issued in App. No. 2,882,013 dated Dec. 14, 2015.
Canadian Office Action issued in App. No. 2,882,013 dated Nov. 1, 2016.
Chinese Office Action issued in App. No. 201510073954.X dated Jan. 12, 2016 (w/ translation).
Chinese Office Action issued in App. No. 201510073954.X dated Sep. 29, 2016.
Extended European Search Report issued in App. No. 15000393.7 dated May 21, 2015.
European Office Action issued in App. No. 15 000 393.7 dated Jun. 17, 2016.
Korean Office Action issued in App. No. 10-2015-0021117 dated Feb. 26, 2016 (w/ translation).
Taiwanese Office Action issued App. No. 104104740 dated Jan. 8, 2016 (w/ translation).
U.S. Office Action issued in U.S. Appl. No. 14/620,714 dated Oct. 2, 2015.
U.S. Office Action issued in U.S. Appl. No. 14/620,714 dated Mar. 25, 2016.
Chinese Office Action issued in App. No. 201510073954.X dated Jan. 13, 2017 (w/ translation).
Taiwanese Office Action issued in App. No. 105109514 dated Feb. 21, 2017 (w/ translation).
Canadian Office Action issued in App. No. 2,924,896 dated Feb. 20, 2017.
Chinese Office Action issued in Appln. No. 201510073954.X dated Apr. 26, 2017 (w/ translation).

* cited by examiner

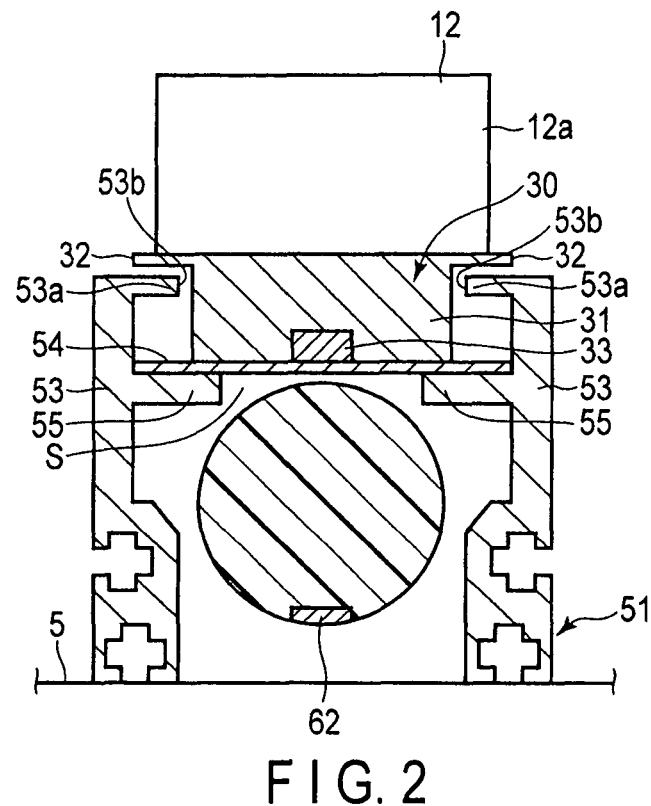
F I G. 2
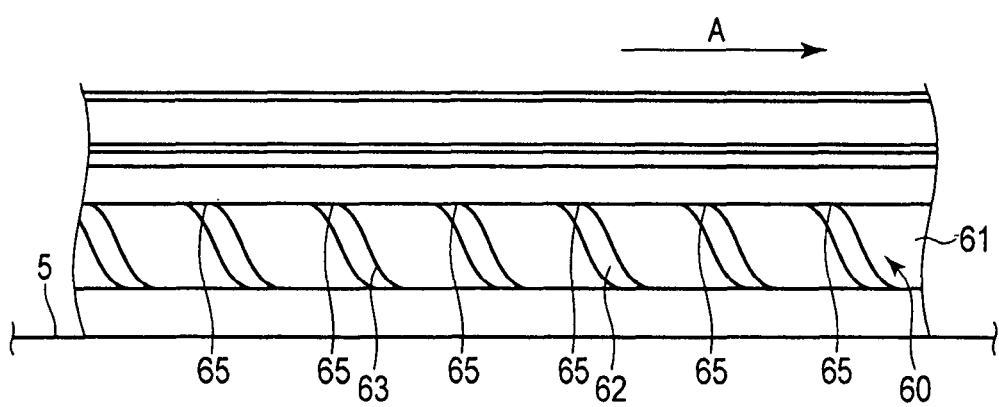
F I G. 3

CONVEYING DEVICE

CROSS-REFERENCE TO RELATED APPLICATIONS

This application is based upon and claims the benefit of priority from Japanese Patent Application NO. 2015-072929, filed Mar. 31, 2015, the entire contents of which are incorporated herein by reference.

BACKGROUND OF THE INVENTION

Field of Invention

The present invention relates to a conveying device for conveying an object to be conveyed such as food items.

Description of Related Art

As a conveying device for conveying an object to be conveyed such as specimens, a conveying device using a conveying belt is known. This type of conveying device comprises a carrier on which a conveyed object is placed, a conveying passage which guides conveyance of the carrier, a conveying belt provided on the conveying passage and on which the carrier is installed, and a drive unit which drives the belt.

The belt driving device rotates the belt to move in its circumferential direction. By rotating the belt, an object to be conveyed is conveyed. This type of technique is disclosed in Japanese Patent No. 4522463.

In a conveying device which conveys a conveyed object such as specimens by using a conveying belt mentioned above, there were the following problems. In the case of conveying a plurality of conveying objects, a plurality of carriers are installed on the conveying belt.

In some cases, in order to apply treatment on a particular object among a plurality of conveying objects, the movement of the particular object is suspended. For example, by applying a stopper to a carrier on which the particular conveyed object is placed, the movement of the particular conveyed object is suspended. However, in order to convey the other conveying objects, the belt remains in a rotating state.

Therefore, friction will occur between the suspended carrier and the belt. Since the belt is formed from, for example, resin, which has flexibility, the belt is subject to abrasion by the friction occurring between the carrier and the belt. As the belt abrades away, the durability of the conveying device is degraded.

Furthermore, in the case where the conveyed object is liquid, if the conveyed object spills, there is a possibility that the conveyed object may run down onto the belt. In this case, interference with the belt and the drive unit rotating the belt may occur, deteriorating cleaning efficiency.

BRIEF SUMMARY OF THE INVENTION

The conveying device of the present invention comprises a carrier comprising a holder side member, a conveying passage guiding conveyance of the carrier, a spirally-shaped spiral member arranged below the carrier and extending along the conveying passage, the spiral member between the spiral member and the holder side member causing a first force which acts in a direction away from the holder side member or a second force which acts to draw in the holder side member, a partition wall portion provided between the carrier and the spiral member, and partitioning the carrier and the spiral member, and a rotary unit rotating the spiral member axis-wise thereof.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view showing a straight conveying passage, a rotary member, and a carrier of the conveying device.

FIG. 3 is a cross-sectional view showing a state in which the straight conveying passage is cut along a cross section along a longitudinal direction of the straight conveying passage.

DETAILED DESCRIPTION OF THE INVENTION

Figure 1:
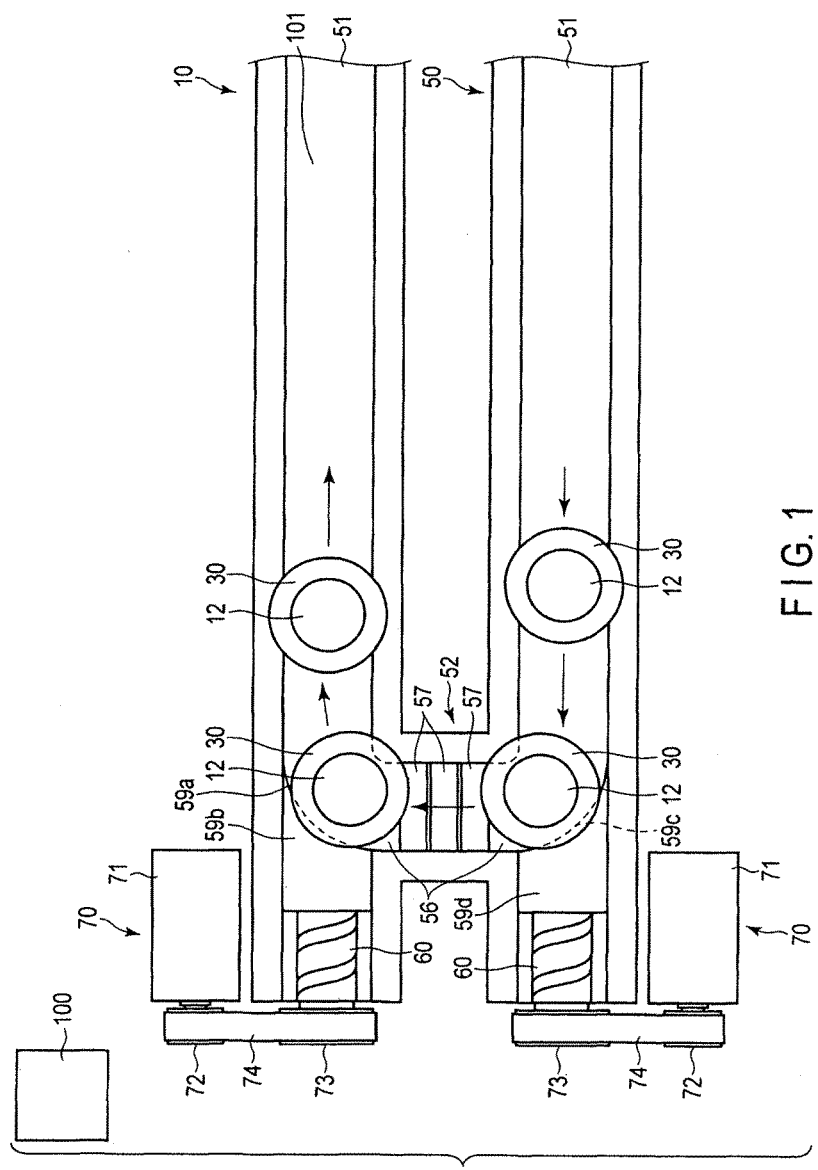
FIG. 1 is a plan view showing a conveying device according to a first embodiment.

A conveying device 10 according to a first embodiment of the present invention will be explained using FIGS. 1 through 3. FIG. 1 is a plan view showing a part of the conveying device 10. As shown in FIG. 1, the conveying device 10 is configured to be capable of conveying a conveyed object 12. For example, the conveyed object 12 comprises a container 12a which opens at the top and with food items contained in the container 12a.

The conveying device 10 comprises a plurality of carriers 30 on which the conveyed object 12 is placed, a conveying passage 50 which guides the conveyance of the carriers 30, a rotary member 60, a driving device 70 which rotates the rotary member 60, and a controller 100.

FIG. 2 is a cross-sectional view showing a part of the conveying device 10. In FIG. 2, the conveyed object 12 is not cut. As shown in FIG. 2, the carrier 30 comprises a cylindrically formed base part 31 and a plate-shaped extending portion 32 formed on an edge part at one end in an axial direction of the base part 31 and protruding outwards in a radial direction with respect to a circumferential surface of the base part 31. A magnet 33 is provided at the bottom of the base part 31. In the present embodiment, for example, the magnet 33 is embedded into the bottom of the base part 31.

As shown in FIG. 1, the conveying passage 50 comprises a pair of straight conveying passages 51 formed linearly and arranged in parallel, and a connecting conveying passage 52 which is connected to both straight conveying passages 51 and is configured to communicate one of the straight conveying passages 51 with the other. The conveying passage 50 is arranged on a floor surface 5.

FIG. 2 shows a state in which the straight conveying passage 51 is cut. As shown in FIG. 2, the straight conveying passage 51 comprises a pair of side wall portions 53 which extends in a longitudinal direction and is arranged to face each other, and a partition wall portion 54 provided between both side wall portions 53.

Between the side wall portions 53 is arranged a gap in which the carrier 30 can be arranged. An upper edge part 53a of the side wall portion 53 protrudes towards the other side wall portion 53. Between the distal ends 53b of the upper edge parts 53a is a gap enabling a base part 31a of the carrier 30 to be movably arranged. Specifically, the gap between the upper edge parts 53a is slightly larger than the diameter of the base part 31a. Also, on the side wall portions 53 are formed protruding portions 55, on which the partition wall portion 54 can be fixed. The protruding portions 55 protrude towards the other side wall portions 53.

The partition wall portion 54 is fixed on the upper end surfaces of both protruding portions 55. The partition wall portion 54 extends from one of the side wall portions 53 to the other side wall portion 53. The partition wall portion 54 is formed plate-shaped extending along the side wall portions 53. The gap between the protruding portions 55 is covered by the partition wall portion 54.

As shown in FIG. 1, the connecting conveying passage 52 extends from one of the straight conveying passages 51 to the other straight conveying passage 51, and is formed in a manner capable of conveying the carrier 30 from one of the straight conveying passages 51 to the other straight conveying passage 51.

Specifically, a cutout 56 is formed at a portion higher than the partition wall portion 54 of the straight conveying passage 51. A plurality of cylindrical rollers 57 for conveying are arranged between the cutout 56 of one of the straight conveying passages 51 and the cutout 56 of the other straight conveying passage 51.

The rollers 57 are arranged so that the upper end thereof is coplanar with the upper end of the partition wall portion 54 of one of the straight conveying passages 51 and the upper end of the partition wall portion 54 of the other straight conveying passage 51, in a manner that the axis line thereof is orthogonal to the direction in which the carrier 30 is conveyed from the one of the straight conveying passages 51 to the other straight conveying passage 51. The roller 57 is rotated by an electric motor, etc.

One of the straight conveying passages 51 is provided with a guide portion 59b which comprises an arc portion 59a for guiding the carrier 30 to enter the connecting conveying passage 52 from the straight conveying passage 51. The other straight conveying passage 51 is provided with a guide portion 59d comprising an arc portion 59c for guiding the carrier 30 to enter the other straight conveying passage 51 from the connecting conveying passage 52.

FIG. 3 is a cross-sectional view showing a state in which the conveying passage 50 is cut along the cross-sectional line along the longitudinal direction of the conveying passage 50. As shown in FIG. 3, the rotary member 60 comprises a cylindrical rotary member main body 61 and a spiral member 62 which is installed in the rotary member main body 61.

As shown in FIG. 2, the carrier 30 is placed on the partition wall portion 54 so that the magnet 33 faces the rotary member 60. The extending portion 32 of the base part 31 overlaps vertically with the top rim 53a of the side wall portion 53.

The rotary member main body 61 is formed from resin which is an example of a material having insulation properties. The rotary member main body 61 is rotatably supported in the straight conveying passage 51 axis-wise. For example, at one end portion of the straight conveying passage 51 is provided a support unit for rotatably supporting the rotary member main body 61.

A spiral groove 63 formed spirally and axis-wise of the rotary member main body 61 is formed on a circumferential surface part of the rotary member main body 61. The spiral groove 63 has a concaved shape with respect to the circumferential surface of the rotary member main body 61. The spiral groove 63 extends from one end to the other end of the rotary member main body 61.

The spiral member 62 is formed from a material having a property which is drawn to the magnet 33 by the magnetic force of the magnet 33. For example, the spiral member 62 is formed from steel as the chief material. The spiral member 62 is arranged in the spiral groove 63 of the rotary member main body 61. The spiral member 62 extends from one end to the other end of the rotary member main body 61.

The rotary member main body 61 and the spiral member 62 are arranged at a position where they would not come in contact with the side wall portions 53 and the partition wall portion 54 when they are rotated axis-wise of the rotary member main body 61.

As shown in FIG. 1, the driving device 70 comprises a driving electric motor 71, a first pulley 72 which is fixed integrally to an output axis of the electric motor 71 in a rotatable manner, a second pulley 73 which is fixed integrally to the rotary member main body 61 in a rotatable manner, and a transmission belt member 74 which is wound around the pulleys 72 and 73.

The electric motor 71 is arranged near one end of the conveying passage 50 on the outside of the conveying passage 50. The second pulley 73 is fixed coaxially to one end of the rotary member main body 61. The second pulley 73 is arranged adjacent to the first pulley 72. The belt member 74 is wound around the pulleys 71 and 72 and formed in a manner capable of transmitting the rotation of the first pulley 72 to the second pulley 73.

The operation of the conveying device 10 will be explained in the following. For example, an operator places the conveyed object 12 on the carrier 30 installed on the conveying passage 50. When the conveyed object 12 is accommodated on the carrier 30, the controller 100 drives the electric motor for driving the roller 57 and the electric motor 71 of the driving device 70.

When the electric motor 71 is rotated, the first pulley 72 rotates. The rotation of the first pulley 72 is transmitted to the second pulley 73 by the belt member 74. The second pulley 73 is rotated by the belt member 74. By rotating the second pulley 73, the rotary member 60 is rotated axis-wise.

By rotating the rotary member 60, the spiral member 62 is rotated. When the spiral member 62 is rotated axis-wise, the portion at the upper end of the spiral member 62 seems, in appearance, to advance in a conveying direction A. The portion at the upper end is not a given portion, it is a portion that appears at the upper end when the spiral member 62 is rotated, which would be referred to as an upper end portion 65. Actually, the spiral member 62 only rotates axial-wise; therefore, the upper end portion 65 does not actually advance along the conveying direction A. The upper end portion 65 is a portion that comes close to the magnet 33 in the spiral member 62.

As the top portion 65, in appearance, advances along the conveying direction A, the carrier 30 is drawn to the upper end portion 65 by the magnetic force of the magnet 33. As a result, the carrier 30 is conveyed along the conveying passage 50.

The carrier 30 that has arrived at the connecting conveying passage 52 from the straight conveying passage 51 comes in contact with the arc 59c of the guide portion 59d, and is guided onto the roller 57 by the arc 59c. As the roller 57 rotates, the carrier 30 is conveyed to the other straight conveying passage 51. The carrier 30 that has arrived at the other straight conveying passage 50 passes through the cutout 56 and moves onto the partition wall portion 54. The carrier 30 that has been moved onto the partition wall portion 54 is conveyed by being drawn to the upper end portion 65 of the spiral member 62 by the rotation of the rotary member 60.

In the conveying device 10 configured in this manner, the rotary member 60 and the carrier 30 are partitioned by the partition wall portion 54. Therefore, even if the food items accommodated in the container 12a are spilled, the spilled food items would not run down onto the rotary member 60. Furthermore, since the spilled food items would accumulate on the partition wall portion 54, the spilled food items may be easily cleaned. Therefore, cleaning may be done efficiently.

By forming the spiral member 62 from a metal material mainly including steel which is cheap and comparatively easy to process, the conveying device 10 may be prepared comparatively easily.

The conveying device 10 does not have a structure using a conveying belt. Specifically, it does not have a structure in which a carrier is installed on an endless shaped conveying belt and conveyed by rotating the belt. The conveying belt is formed from resin etc., which has flexibility. Therefore, if friction occurs between the carrier 30 and the belt by stopping a particular carrier 30 on the belt, the belt will abrade away by this friction. As the belt abrades away, the durability of the conveying device will be degraded.

In the conveying device 10 of the present embodiment, without using the conveying belt, the conveyed object placed on the carrier 30 comprising the magnet 33 is conveyed in accordance with the rotation of the spiral member 62. In this manner, since a conveying belt which abrades away comparatively easily is not used, the durability of the conveying device 10 can be improved.

A conveying device 10A according to the second embodiment will be explained using FIG. 4. For the configurations similar to those of the first embodiment, the same reference symbols as used in the first embodiment will be used, and the explanations thereof will be omitted.

Figure 4:
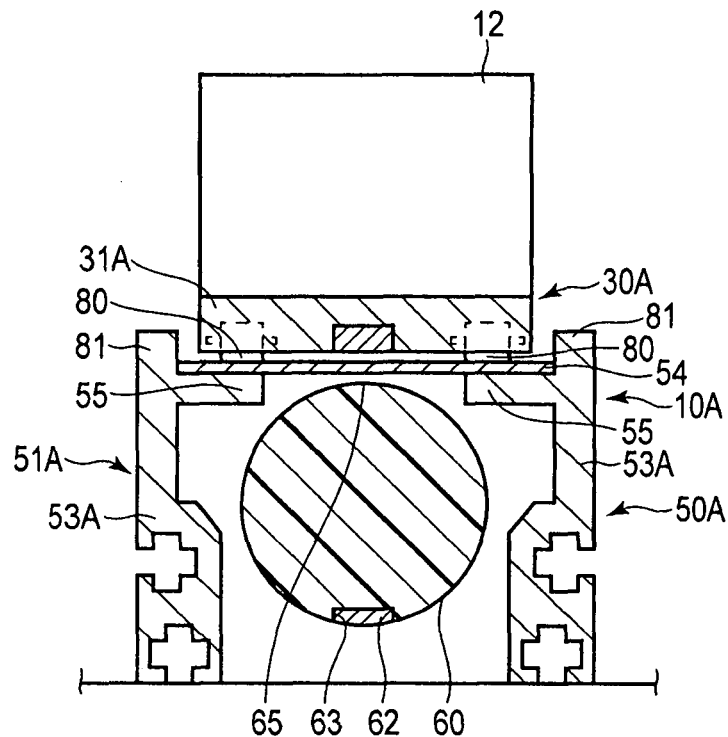
FIG. 4 is a cross-sectional view showing a state in which a straight conveying passage, a rotary member, and a carrier of a conveying device according to a second embodiment is cut.

FIG. 4 is a cross-sectional view showing a part of the conveying device 10A being cut. As shown in FIG. 4, the conveying device 10A comprises a carrier 30A, a conveying passage 50A, a rotary member 60, and a driving device 70.

FIG. 4 is a cross-sectional view showing a straight conveying passage 51A of the conveying passage 50A and the carrier 30A. As shown in FIG. 4, the carrier 30A comprises a cylindrical base part 31A and a wheel 80 formed on the base part 31A. A plurality of wheels 80 are provided to stabilize the posture of the base part 31A. A plurality of wheels 80 are supported rotatably at the bottom portion of the base part 31A. The lower end of the wheel 80 is positioned lower than the bottom surface of the base part 31A.

The conveying passage 50A comprises a straight conveying passage 51A and a connecting conveying passage 52. The straight conveying passage 51A comprises side wall portions 53A which are arranged opposite to each other and a partition wall portion 54. The side wall portions 53A are arranged with a gap enabling the carrier 30 to be arranged therebetween. Protruding portions 55 are formed on the side wall portions 53A, from which they protrude toward each other. The side wall portions 53A comprise protruding portions 81 which are formed to protrude above the partition wall portion 54 to prevent the carrier 30 from falling off the partition wall portion 54.

The carrier 30A is placed on the partition wall portion 34 in a manner that the rotary axis of the wheel 80 is orthogonal to the conveying direction of the carrier 30A. When the carrier 30A is conveyed, the wheels 80 rotate.

The conveying device 10A configured in this manner has an effect similar to that of the first embodiment. In the conveying device 10A of the present embodiment, the rotation of the wheel 80 allows the carrier 30A to be conveyed smoothly.

Even if the carrier 30 moves in the width direction on the partition wall portion 54, the carrier 30 will abut the protruding portion 81 and be prevented from falling off the partition wall portion 54.

A conveying device 10B according to the third embodiment of the present invention will be explained using FIG. 5. For the configurations similar to those of the first embodiment, the same reference symbols as used in the first embodiment will be used, and the explanations thereof will be omitted.

A conveying device 10B comprises a carrier 30B, a conveying passage 50B, a rotary member 60, and a driving device 70.

Figure 5:
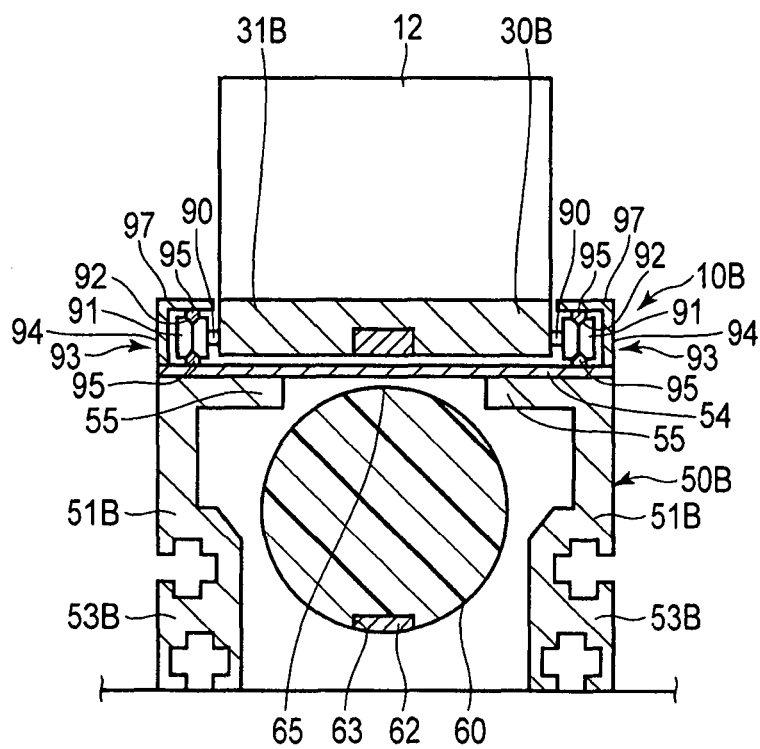
FIG. 5 is a cross-sectional view showing a state in which a straight conveying passage, a rotary member, and a carrier of a conveying device according to a third embodiment is cut.

FIG. 5 is a cross-sectional view showing a straight conveying passage 51B of the conveying passage 50B, the carrier 30B, and the rotary member 60. As shown in FIG. 5, the carrier 30B comprises a cylindrical base part 31B, a rotary axis 90 formed on the base part 31B, and wheels 91 which are rotatably supported by the rotary axis 90.

The rotary axis 90 penetrates the base part 31B, and both ends thereof protrude outwards from the circumferential surface of the base part 31B. A plurality of rotary axes 90 are provided. The wheels 91 are rotatably supported on one each of both ends of the rotary axes 90. A concaved part 92 which is concaved from the other portion is formed on the center portion of the wheel 91 along the rotary axis of the outer circumference surface thereof.

The conveying passage 50B comprises the straight conveying passage 51B, a connecting conveying passage 52, and a guide device 93. The straight conveying passage 51B comprises side wall portions 53B which are arranged opposite to each other and a partition wall portion 54. The side wall portions 53B are arranged with a gap enabling the carrier 30B to be arranged therebetween. The protruding portions 55 are provided at upper edge parts of the side wall portions 53B.

The guide device 93 comprises accommodating portions 94 which are provided on each of the edge parts on both ends in the width direction of the partition wall portion 54, and a pair of guide rails 95 which are installed in the accommodating portions 94. The accommodating portions 94 extend along the side wall portions 53B. The accommodating portions 94 comprise plate-shaped side wall portions 96 which stand upwards with respect to the partition wall portion 54, and plate-like upper wall portions 97 which extend from the upper end edges of the side wall portions 96 toward the side wall portions 53B on the other side.

The guide rails 95 are fixed facing each other on each of the lower surface of the upper wall portion 97 and the upper surface of the partition wall portion 54. The guide rails 95 extend along the upper wall portion 97 and the partition wall portion 54, on which the concaved part 92 of the wheel 91 is engageably formed.

The guide device 93 is not provided at a portion where the connecting conveying passage 52 is connected at the straight conveying passage 51B.

The carrier 30B is placed on the partition wall portion 34 in a manner that the rotary axis 90 is orthogonal to the conveying direction of the carrier 30B. The wheel 91 is engaged with the guide rail 95 provided on the partition wall portion 34 and the guide rail 95 provided on the upper wall portion 97 by the concaved part 92. More specifically, the wheel 91 is arranged between the guide rails 95. When the carrier 30B is conveyed, the wheel 91 rotates on the guide rails 95.

When the base part 31B is placed on the straight conveying passage 50B, in other words, when the wheel 91 is placed between the pair of upper and lower guide rails 95 and is engaged with the guide rails 95 by the concaved part 92, the position of the rotary axis 90 is provided at a position where a gap is left between the bottom surface of the base part 31B and the partition wall portion 54. Therefore, the bottom surface of the carrier 30B does not scrape the partition wall portion 54.

The conveying device 10B configured in the above manner may obtain the same effect as in the first embodiment. Since the carrier 30B comprises a wheel 91, the carrier 30A may be conveyed smoothly. By engaging the wheel 91 with the guide rail 95, the carrier 30B will be conveyed smoothly along the guide rail 95.

The present invention is not limited to the first to third embodiments. In the first to third embodiments, as an example of a means to draw the carrier 30 to the spiral member 62 of the rotary member 60, the spiral member 62 has been formed from steel as its chief material, and the magnet 33 has been placed in the carrier 30.

In this manner, the magnet 33 and a metal which is drawn to the magnet have been used. As another example, the spiral member 62 may be formed from a magnet as its chief material, and the carrier 30 may be provided with a material which is drawn to the spiral member 62 such as a metal material.

The spiral member 62 may also be formed from a magnet, and may provide the magnet that draws the spiral member 62 in the carrier 30. Alternatively, the spiral member 62 may be formed from a magnet. In this manner, the spiral member 62 may be formed entirely from a magnet, or may have a magnet partially provided therein.

In other words, in order to move the carrier 30 in accordance with the movement of the spiral member 62, one of the two materials which have properties of being drawn to each other should be used to form the spiral member or should be partially provided on the spiral member, and the other material should be provided on the carrier 30.

Alternatively, one of the two materials having properties of being repulsive to each other may be provided in the carrier 30, and the other may be used to form the spiral member 62, or may be partially provided on the spiral member 62. As an example of this structure, a pair of magnets repulsive to each other may be given. According to this structure, when the upper end part 65 of the spiral member 62 appears to move, the carrier 30 moves by the repulsive force acting between the magnets.

In the first to third embodiments, one rotary member 60 is used; however, the invention is not limited to this. For example, a plurality of rotary members 60 may be aligned in series along with the conveying passage 50.

The conveyed object is not limited to food items. For example, the conveyed object may be a specimen of blood, etc., cardboard, an electric appliance, various devices, and various machines.

The shape of the carrier 30 is not limited. The carrier 30 may be formed to comply with the shape of the conveyed object. For example, in the case where the conveyed object is a test tube accommodating a specimen of blood etc., the carrier may be formed in a shape capable of keeping the test tube standing.

Therefore, it is to be noted that the present invention is not limited to the above-described embodiments, and can be provided by modifying the constituent elements without departing from the gist in the embodiment stages. By combining the plurality of constituent features disclosed in the embodiments as appropriate, various inventions may be formed. For example, some of the constituent features may be deleted from the entire constituent element described in the embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A conveying device comprising:
a conveying passage which comprises a pair of sidewall portions arranged opposite to each other, a first protruding portion provided on each of the sidewall portions and protruding towards each of the other sidewall portions, a partition wall portion provided on the first protruding portion of both of the sidewall portions in a manner covering a gap between the first protruding portions to partition one side from the other side bordering the protruding portion, and a second protruding portion provided on each of the sidewall portions and protruding above the partition wall portion;
a carrier which is arranged on the partition wall portion and comprises a holder side member;
a spirally-shaped spiral member which is arranged lower than the partition wall portion between the sidewall portions, in a manner extending along the conveying passage, the spiral member causing between the spiral member and the holder side member a first force which acts in a direction away from the holder side member, or a second force which acts to draw in the holder side member; and
a rotary unit which rotates the spiral member axis-wise thereof, wherein
the carrier comprises a wheel which comes in contact with an upper surface of the partition wall portion.

* * * * *